(12) United States Patent
Jones

(10) Patent No.: US 10,137,901 B2
(45) Date of Patent: Nov. 27, 2018

(54) INTOXICATED VEHICLE DRIVER ACCIDENT REDUCTION SYSTEM

(71) Applicant: Daniel Jones, Overland Park, KS (US)

(72) Inventor: Daniel Jones, Overland Park, KS (US)

(*) Notice: Subject to any disclaimer, the term of this patent is extended or adjusted under 35 U.S.C. 154(b) by 21 days.

(21) Appl. No.: 15/382,352

(22) Filed: Dec. 16, 2016

(65) Prior Publication Data

US 2017/0096146 A1 Apr. 6, 2017

Related U.S. Application Data

(63) Continuation-in-part of application No. 14/678,619, filed on Apr. 3, 2015.

(Continued)

(51) Int. Cl.
| | |
|---|---|
| *B60K 28/06* | (2006.01) |
| *B60W 40/08* | (2012.01) |
| *B60W 50/08* | (2012.01) |
| *F02D 41/00* | (2006.01) |
| *F02D 41/02* | (2006.01) |
| *F02N 11/10* | (2006.01) |
| *F02P 11/04* | (2006.01) |

(Continued)

(52) U.S. Cl.
CPC ............ *B60W 40/08* (2013.01); *B60K 28/06* (2013.01); *B60K 28/063* (2013.01); *B60W 50/087* (2013.01); *F02D 41/0097* (2013.01); *F02D 41/021* (2013.01); *F02N 11/101* (2013.01); *F02P 11/04* (2013.01); *B60W 2040/0836* (2013.01); *B60W 2540/24* (2013.01); *F02D 17/04* (2013.01); *F02D 2041/281* (2013.01); *F02D 2200/0406* (2013.01); *F02D 2200/60* (2013.01); *F02D 2250/26* (2013.01); *F02D 2400/11* (2013.01); *F02N 2200/10* (2013.01); *F02P 5/1502* (2013.01); *G01N 33/4972* (2013.01)

(58) Field of Classification Search
CPC .......... F02P 5/1502; F02P 13/00; F02P 11/04; F02D 2041/281; F02D 2041/283; F02D 2041/285; F02D 41/26; F02D 41/28; F02D 41/0097; F02D 41/021; F02D 43/00; F02D 45/00; B60W 40/08; B60W 50/087; B60K 28/06; B60K 28/063; F02N 11/101
USPC .......................... 123/480, 647; 701/103, 112
See application file for complete search history.

(56) References Cited

U.S. PATENT DOCUMENTS

| | | | | |
|---|---|---|---|---|
| 4,093,945 A | * | 6/1978 | Collier | ..................... A61B 5/18 180/272 |
| 2010/0121502 A1 | * | 5/2010 | Katayama | ............ B60K 28/063 701/1 |

(Continued)

*Primary Examiner* — Hai Huynh
*Assistant Examiner* — Gonzalo Laguarda

(57) ABSTRACT

A sobriety ignition interlock system including an engine control device and a method for managing available vehicle engine power using the sobriety ignition interlock system. The engine control device includes an engine control processor (ECP) that is electronically connected in between an engine control unit (ECU), an engine sensor assembly, and a sobriety processor. The sobriety processor determines a sobriety level of a vehicle driver and sends a corresponding sobriety signal to the ECP. The ECP intercepts an engine signal transmitted from the engine sensor assembly to the ECU and manipulates the engine signal according to the sobriety signal, in order to manage the available power of the vehicle engine.

19 Claims, 15 Drawing Sheets

Related U.S. Application Data

(60) Provisional application No. 62/123,338, filed on Nov. 14, 2014.

(51) Int. Cl.
    *F02P 5/15*         (2006.01)
    *F02D 17/04*      (2006.01)
    *G01N 33/497*    (2006.01)
    *F02D 41/28*      (2006.01)

(56) References Cited

U.S. PATENT DOCUMENTS

| | | | | |
|---|---|---|---|---|
| 2010/0294583 A1* | 11/2010 | Biondo | ................ | B60K 28/063 |
| | | | | 180/272 |
| 2011/0153367 A1* | 6/2011 | Amigo | .................... | G06Q 40/08 |
| | | | | 705/4 |
| 2012/0188532 A1* | 7/2012 | Li | ........................ | A61B 5/4845 |
| | | | | 356/51 |
| 2014/0309862 A1* | 10/2014 | Ricci | ...................... | G01C 21/00 |
| | | | | 701/36 |

\* cited by examiner

INTOXICATED VEHICLE DRIVER ACCIDENT REDUCTION SYSTEM

The current application is a continuation in part of U.S. patent application Ser. No. 14/678,619 filed on Apr. 3, 2015 which claims benefit of U.S. Provisional Patent Application Ser. No. 62/123,338 filed on Nov. 14, 2014.

FIELD OF THE INVENTION

The present invention relates generally to sobriety testing for vehicle drivers. More specifically, the present invention provides a means for managing available vehicle engine power according to the detected sobriety level of a vehicle driver.

BACKGROUND OF THE INVENTION

Many thousands of drivers convicted of DUI/DWI have been mandated by Judicial Order to have ignition interrupting or engine starter interrupting systems installed on their vehicles to help ensure after verification of their blood alcohol content (BAC) that they do not operate a vehicle while intoxicated. These systems are generally known as BAIIDs (breath alcohol ignition interlock devises).

The field of ignition interlocks is well known; however, today the majority of these devices simply block electrical power to the starter motor but do not inhibit the ignition system at all. The most direct way to stop intoxicated individuals from operating motor vehicles was to prevent the ignition system from providing spark energy to the combustion cylinders. However, diesel engines do not have spark plugs or electronic ignition systems. As more diesel powered passenger vehicles became prevalent, such vehicles could not have a spark ignition system blocked as part of the solution to keep intoxicated drivers off the road, as such vehicles do not contain energized spark plugs. This was one of the reasons that the industry began to only inhibit the starter motor from being provided power to start the engine, when an over the limit, driver BAC was detected.

With improving automotive technology, many ignition systems started to become far more advanced in order to provide more engine power, fuel efficiency, and lower emissions. These highly complex ignition systems started including multiple ignition coils, multiple spark patterns, highly varied timing routines, and a complex interface with modern engine control units (ECUs), the engine's main computer. Most vehicles now have computer controlled engines that are integrated with advanced ignition systems. So there is not just one ignition power wire to simply interrupt, as emissions and ECUs can malfunction.

Further, some new vehicles now also employ fully integrated remote start systems at time of factory production into many new models. This complicates the connection between a BAIID engine control box and these highly sophisticated ignition systems.

Another significant problem today is that BAIIDs only stop the engine from starting. So in the event that the driver is just below the threshold limits at engine start up, then the driver is fully able to drive in an unconstrained manner if the driver continues to ingest alcohol. Once the engine is started, the starting system cannot limit or reduce the danger of an intoxicated driver operating a motor vehicle.

Another significant problem is that currently available BAIIDs only prevent the engine from starting. So the BAIID could measure a BAC just below the threshold limit and allow engine starting, but previously consumed alcohol may continue to enter the driver blood stream, thereby increasing intoxication while driving. Additionally, the driver may have passed a BAC measurement prior to starting the engine, but may consume alcohol and drive the vehicle. The systems on the market today are required, by law, to re-test periodically but no action is taken to incrementally or systematically reduce engine power or slow the vehicle; just to record the illegal event. Accordingly, the intoxicated driver is allowed to continue driving on the public roads and highways.

It is commonly known that speed kills and with more speed, the more adverse the consequences can and may be, especially when a driver is intoxicated. An impaired driver is more likely to compound the severity of an accident than a sober driver. An impaired driver generally has far less ability to take at least some corrective actions so as to mitigate the impact energy, direction of travel, and likelihood of involving more vehicles and pedestrians in a collision.

Additionally, if an intoxicated individual fails a re-test in a BAIID equipped vehicle, the driver may be less likely to properly process the punitive consequences of continuing to drive. Due to the nature of these drivers' ability to reason, every day hundreds of intoxicated drivers continue to drive even with failed re-tests.

Convicted drivers who are willing to ignore a failed re-test, may be more likely to become repeat offenders. As such, intoxicated drivers may not have the state of mind to prioritize much more than their immediate circumstances, and are more likely to ignore other related laws and regulations.

More importantly, a group of convicted drivers that are failing or willfully refusing a re-test are generally more likely to have been convicted of DUI/DWI several times. As a convicted driver, and again disregarding the law, there is a much stronger incentive for them to actually speed up so as to more quickly get to their destination and avoid getting caught in the act.

Accordingly, with increased speed, combined with intoxication, the nature and impact to the public safety is exponentially compounded. Convicted drivers that are again intoxicated and risking significant fines and imprisonment, could be some of the most dangerous and lethal drivers on the road.

The advent and technological advancements of BAIIDs over the last number of years has inarguably helped to incentivize tens of thousands of drivers to stop driving while intoxicated. But without the ability to do more than just warn these drivers through electronic means, more lives are at greater risk of death and severe injury.

In addition, there have been a number of attempts, some cited by the inventor, to incorporate BAIIDs in conjunction with speed limiting and engine power reduction functions. However, these systems have been too costly, complex, or even have required monitored call control centers staffed with personnel to assist with every driver that has not fully complied with measured BAC levels. Accordingly, such BAIID systems are not commercialized and available to assist in the public interest.

The prior art in this field however does disclose considerable quantities of highly detailed apparatus and methodology concerning the enablement of the determination of driver BAC levels and highly detailed and critically important event recording systems. These significantly advanced and evolved BAC measuring, monitoring and recording systems allow specially trained and certified staff and monitoring installation centers to closely track attempts made by drivers required to use a BAIID. However, there are very minimal and sometimes no enablement specifications described in prior art systems that suggest an attempt to actually control engine functionality as a cost effective bolt on system.

Many prior art references simply suggest "some" connection with the vehicle's air intake, fuel system, or engine control module's service port. Some prior art provides limited detail of operational function concerning the air intake or fuel systems, but most have just considered connecting to a significant and complex vehicle air induction, fuel or computerized control system without regard to the nature of these system's critically complex and uniquely formatted flow capacities and geometries as they relate to the many dozens of different vehicle engine families and in cooperation with dozens of unique vehicle manufacturers worldwide.

The field of this invention is for BAIIDs that are installed on a wide variety of vehicles and as an aftermarket accessory and generally on a temporary basis. They are installed for a term of months to several years, as determined by judicial order. At the time in which this term ends, they are removed and may be installed on another vehicle for the same purpose. The prior art simply does not allow compliance staff and facilities to affordably and quickly install aftermarket installations of BAIIDs and then allow their easy removal, with no damage or harm to the vehicle, its engine, drive train, or emissions systems.

SUMMARY OF THE INVENTION

What is needed is an improved breath alcohol ignition interlock device (BAIID) that can be easily installed as aftermarket equipment and then be easily removed, which can prevent engine starting and also reduce engine power.

An improved BAIID that will block a spark ignited or compression ignited diesel engine from starting if a driver does not pass the blood alcohol content (BAC) pre-set threshold. An improved BAIID not only reliant on interrupting power to the starter motor, as vehicles can be push started.

An improved BAIID that will block gas, spark ignited engines from starting and that is not reliant on interrupting the engine's ignition system directly by blocking current to it. This, as ignition systems now may require multiple connections, and may also contain remote start features.

An improved BAIID that has the ability to control various engine power parameters as driver intoxication is detected in a re-test, and based on pre-determined thresholds of power reduction, that will promote far greater levels of public safety.

An improved BAIID that does not require the removal, modification, or manipulation of the vehicle air intake system, and the need for a compliance facility to inventory many dozens of air intake systems, hardware, and highly specialized components.

An improved BAIID that does not require a complex and costly aftermarket secondary air throttling system requiring a computerized actuator motor, an integrated valving system, and an integrated electronic control system for this purpose.

An improved BAIID that does not require the disconnection, modification or manipulation of a high pressure automotive fuel system, and the need for a compliance facility to inventory many dozens of fuel valving systems, hardware and highly specialized components.

An improved BAIID that does not require a complex and costly aftermarket fuel throttling system requiring a computerized actuator motor and integrated electronic control system to reduce fuel supply directly.

An improved BAIID that does not require the removal of a vehicle transmission and costly components, and intensive labor to install and uninstall these highly specialized components, and that does not require a compliance facility to inventory hardware and highly specialized equipment and components for many dozens of vehicle platforms.

My invention consists of a new and novel engine management control system in combination with a BAIID that is used to limit or change the operating power output of any engine that is equipped with original equipment manufacturer (OEM) engine sensors, and those specific to emissions controlled spark ignited or diesel engines, which are on the vast majority of vehicles on the roads today.

Referenced attempts and other prior art that throttles or governs power output of an internal combustion engine have suggested additional intake air throttle systems, inline fuel restriction valving systems, and electronic voltage or signal control to fuel pumps, so as to reduce fuel, and resulting engine power, when commanded.

However these, as would be incorporated into a BAIID, would require elaborate air intake systems and/or very precise, fuel interface variable restriction systems and equipment which would add significant cost and significant time to install on any of the thousands of vehicles that are required to have a BAIID installed. Simply limiting fuel supply alone provides a lean combustion air fuel ratio and can and may cause significant engine damage.

The present invention instead uses an "engine control processor", hereto referenced as an "ECP" unit. This inventive microprocessor control unit contains wiring provisions specific to each vehicle engine platform, and that vary by year, make, and manufacturer.

This ECP is constructed and programmed specifically for each engine platform, so that all desired engine power and revolutions per minute (RPM) reductions are produced by the input values of any of a number of engine sensors, alone or in combination. The ECP calculating the appropriate modified electronic outputs so as to achieve the desired engine performance and characteristics.

Contained within each and every emissions equipped and controlled vehicle that is legally sold in the United States and which complies with the Environmental Protection Agency (EPA), are many necessary and unique electronic sensors and meters. These sensors and meters help the engine control unit (ECU), or engine computer, make decisions thousands of times a second. So the ECU is integrally involved each and every time any emissions controlled vehicle, either spark ignited or compression ignited, is started or operated, and 100% of the time the engine is running.

However, what was not known is that with the new and unique methods of the present invention, manipulation and changes to these signal outputs of these certain engine sensors by the ECP, allow the function and power of the engine to be controlled with a high degree of precision without affecting engine reliability. And no matter to what degree the intoxicated driver attempts to gain greater speed by opening the throttle pedal, these highly synchronized sensor signal manipulations communicate the appropriate series of coordinated input signals to the engine's ECU, so as to reduce power and RPM in accordance with pre-determined parameters and guidelines.

This degree of precision is in many ways similar to that of standard and known engine controls such as intake air throttles, and ignition switches to turn on or off an engine, however the present invention requires no physical hardware which actually restricts intake air, fuel supply, or changes the transmission gear ratio.

The present invention simply connects to existing sensors, and therefore is "plug and play". By unplugging an existing engine sensor, and plugging in an input wire harness from the ECP, my ECP contains an identical wire harness that directly plugs into the factory equipped wire harness that originally plugged into a particular sensor as above. Multiple sensors can be employed for advanced function or, dependent on particular engine family and its factory operating system, in some cases one sensor can provide the needed blocking of engine starting and power reduction after start up.

The scope of the present invention may or may not include the use of the following sensors, but is not limited to the use of additional or other sensors not listed or included in the following: a mass air sensor, crankshaft position sensor, camshaft position sensor, throttle position sensor, manifold pressure sensor, air intake temperature sensor, ambient air temperature sensor, coolant sensor, or engine oil temperature sensor.

My invention continuously monitors sensor output when an engine is started or running by reading the electronic output data supplied by the mass air sensor, and/or the crankshaft or camshaft sensors, or other sensors. Crankshaft position sensors are equipped on all emissions controlled, and even most non-emissions controlled, electronic fuel injected vehicles; this includes spark ignited or compression ignited internal combustion engines.

The ECP is continually reading the engine RPM of the engine; even if just a "speed density" system, and not the more modern mass air sensor fuel injection systems. The ECP can utilize either several of these sensors in combination or separately, and in addition can substitute a camshaft position sensor as opposed to a crankshaft position sensor, to determine engine RPM at all times.

A preferred first step of operation for the ECP is to determine engine speed, and this also determines if the engine is running at all. Reading engine speed from the output signal of a crankshaft or camshaft position sensor provides the ECP real time engine RPM. And in combination, reading the mass air sensor output signals correlates directly to approximated engine horsepower. So in the case that these sensors are used in combination, engine starting can be inhibited by interrupting any speed sensor (CPS) and a lower mass air signal sent to the vehicle's ECU, which cause the ECU to command significantly less fuel to the engine, and reduce engine horsepower.

To inhibit engine starting, in some cases, any of the 3 above sensors can be used depending on engine ECU programming logic. However, other vehicle platforms may be used alone as a single signal from one individual sensor and can provide effective enough manipulated data from the ECP to the ECU that most engines will not be startable.

When there is the desire and need to restrict power and RPM to preset values, these same, as listed above, sensors can be employed alone or in combination, for more precise control of engine power and speed.

These are some of the general parameters of engine operation that the present invention controls:

Inhibit the engine from starting at all. This, most likely in cases when the environmental temperature conditions are not a threat to the driver or vehicle occupants.

Allow the engine to start and idle, but if more power is commanded by an intoxicated driver, so as to drive the vehicle, the ECP can be programmed to shut off the engine before the vehicle is accelerated, or simply limit the engine RPM to idle only.

While driving, if a driver should fail a re-test the ECP can control the engine power and speed in numerous capacities. Such as not to allow the intoxicated driver full and obstructed access to full engine power and acceleration, and to limit speed to just below posted highway maximums for any given jurisdiction.

While driving, if a driver should fail a re-test the ECP can control the engine power and speed in numerous capacities. Such that several sudden and unexpected, hard and momentary losses of power override the stereo or any other distractions that one, especially when intoxicated can be more easily be distracted. These warnings that consist of very momentary and abrupt power losses will send a powerful message to the offending driver. The message that they are no longer in full control of the vehicle, and that the consequence of prosecution and legal penalties should be strongly considered. With this feature, the communication to the driver is being physically reinforced by the vehicle itself and in real time. This is far more compelling than just visible or verbal warning.

While driving, if a driver should fail a re-test, the ECP can control the engine power and speed in numerous capacities. Another aspect of the invention is that the reduction of power and speed may be indexed to BAC above 0.02 and use a sliding scale. So if a driver's BAC is increasing while driving, or failing to take the re-test at all, the vehicle will continue to slow and lose power at a reasoned and predetermined pace. This so as not to cause addition risk or loss of safety to the driver or other individual.

DETAIL DESCRIPTIONS OF THE INVENTION

All illustrations of the drawings are for the purpose of describing selected versions of the present invention and are not intended to limit the scope of the present invention.

Figure 1:
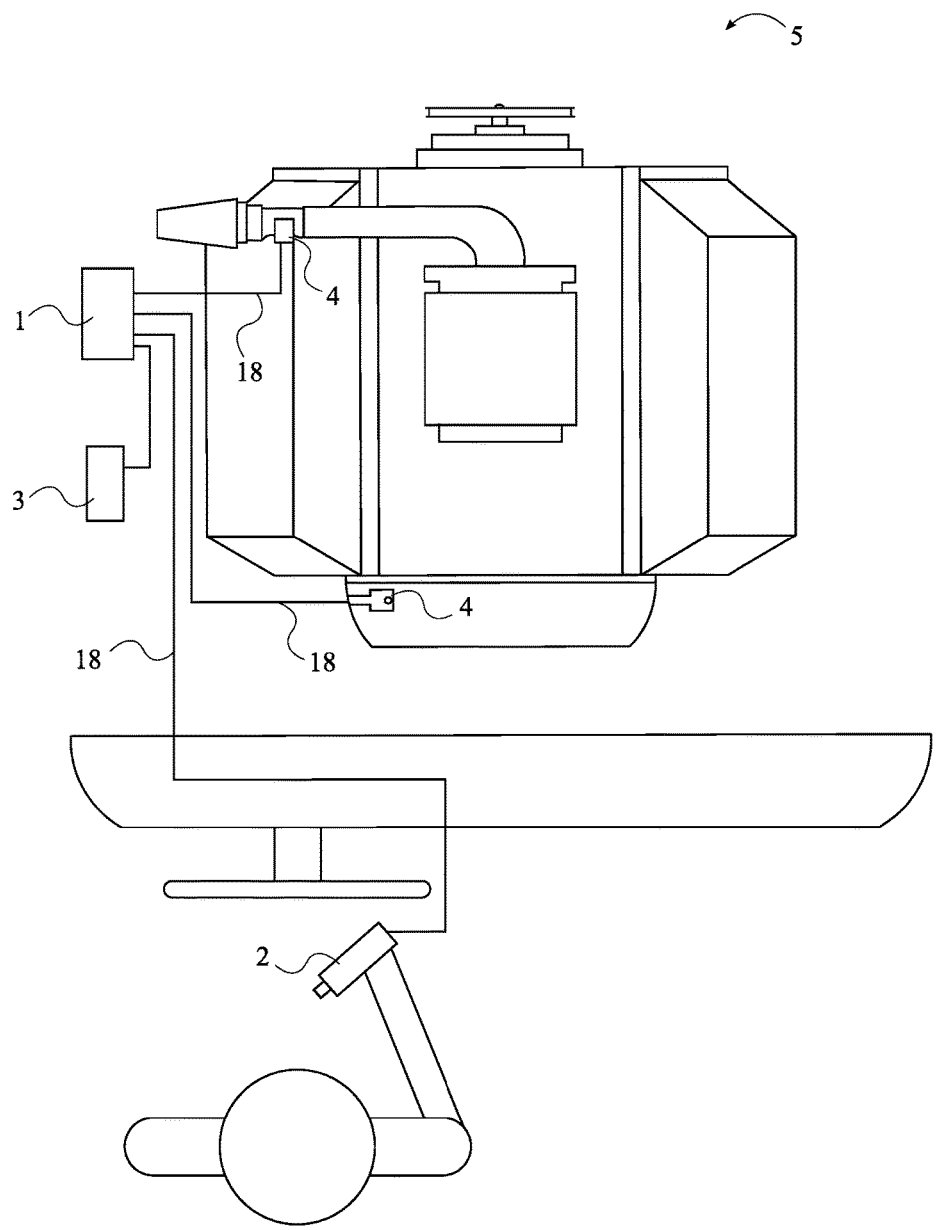
FIG. 1 is a diagram depicting the sobriety ignition interlock system installed within a vehicle, wherein the engine control device is configured to the specific vehicle engine platform in order to communicate with the engine control unit (ECU) and the engine sensor assembly.

The present invention provides a sobriety ignition interlock system including an engine control device 1 and a method for managing available vehicle engine power using the sobriety ignition interlock system. The engine control device 1 can be provided as an aftermarket component for a vehicle, or included in the vehicle at the time of manufacture. The sobriety ignition interlock system further includes an engine control unit (ECU) 3, an engine sensor assembly 4, and a sobriety measuring device 2, as depicted in FIG. 1.

The ECU 3 and the engine sensor assembly 4 correspond to a specific vehicle engine platform 5 and are provided at the time of manufacture. The specific vehicle engine platform 5 is defined by the make and model of the vehicle. There are no standard conventions used amongst automotive companies, and even within a single automotive company, the standards may vary from one model to another. As such, the specifics of the ECU 3 and the engine sensor assembly 4 are dependent on the specific vehicle engine platform 5 and may vary across make and model.

Alternatively, the ECU 3 and engine sensor assembly 4 could be provided as aftermarket replacements for the original equipment manufacturer (OEM) components. For example, the ECU 3 could replace an OEM ECU 3, or the engine sensor assembly 4 could replace an OEM engine sensor assembly 4. Providing the ECU 3 and the engine sensor assembly 4 as aftermarket components would allow for the standardization of the sobriety ignition interlock system; particularly the standardization of the engine control device 1.

The engine control device 1 is the central component of the sobriety ignition interlock system, wherein the engine control device 1 is in communication with the ECU 3, the engine sensor assembly 4, and the sobriety measuring device 2. In reference to FIG. 3, the engine control device 1 comprises a housing 10, an engine control processor (ECP) 12, an electronic input port 14, an electronic output port 16, and a wiring harness 18. The ECP 12 is electronically connected in between the electronic input port 14, the electronic output port 16, and the wiring harness 18, wherein the ECP 12 provides a central hub for sending and receiving electrical signals.

Figure 3:
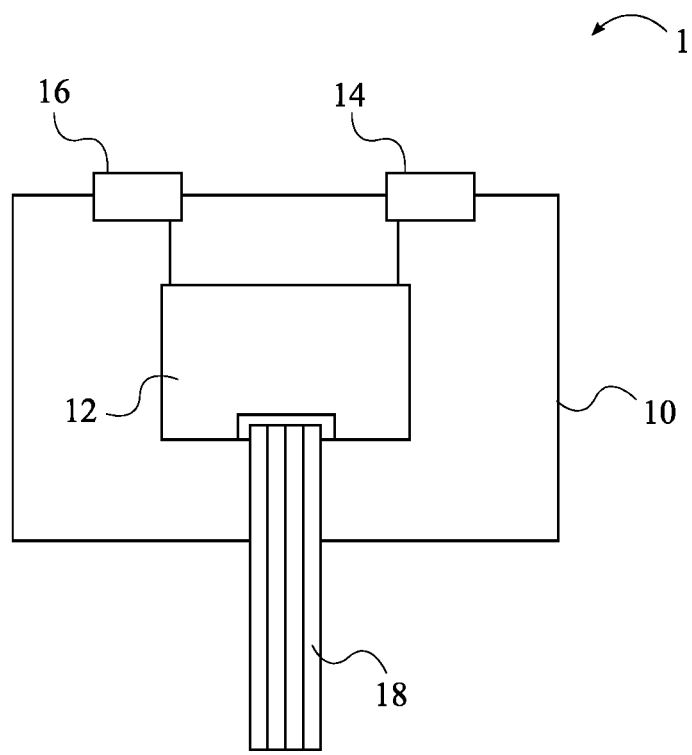
FIG. 3 is a sectional view of the engine control unit, wherein the ECP is positioned within the housing, and both the electronic input port and the electronic output port are mounted into the housing.

In further reference to FIG. 3, the housing 10 of the engine control device 1 supports and houses the electrical components of the engine control device 1. The ECP 12 is positioned within the housing 10, while the electronic input port 14 and the electronic output port 16 are mounted into the housing 10, such that the electronic input port 14 and the electronic output port 16 are accessible about the exterior of the housing 10. Meanwhile, the wiring harness 18 traverses through the housing 10; the wiring harness 18 being terminally connected to the ECP 12 within the housing 10.

Figure 4:
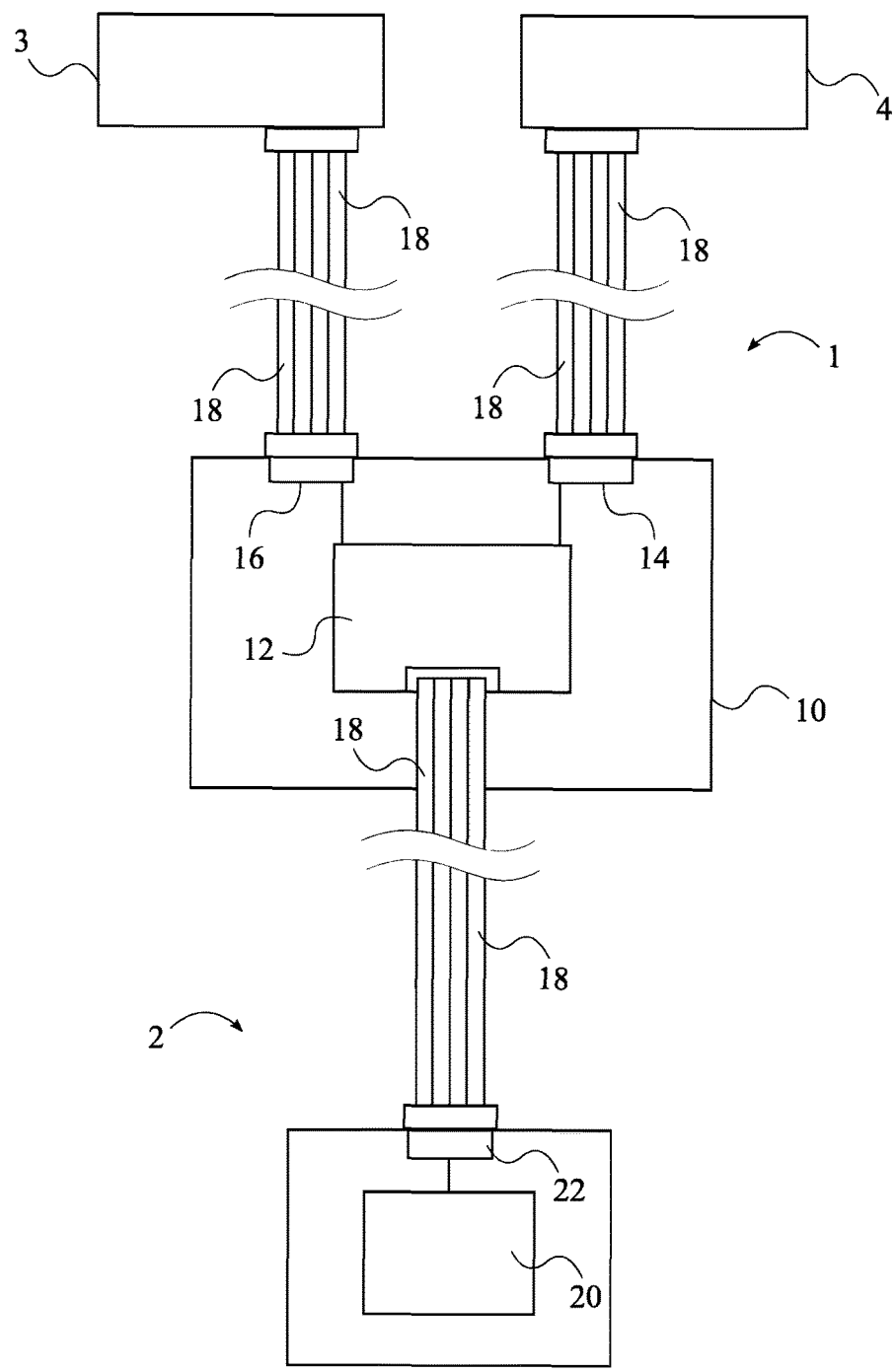
FIG. 4 is a diagram depicting the physical connection between the engine control device and each of the ECU, the engine sensor assembly, and the sobriety measuring device via the respective wiring harness.

In reference to FIG. 4, the electronic input port 14 is configured to connect the engine sensor assembly 4 to the ECP 12, while the electronic output port 16 is configured to connect the ECU 3 to the ECP 12. More specifically, a wiring harness 18 of the engine sensor assembly 4 is terminally connected to the electronic input port 14 and a wiring harness 18 of the ECU 3 is terminally connected to the electronic output port 16. The specific connection type (e.g. the number of pins, arrangement of pins, etc.) between the electronic input port 14 and the electronic output port 16 depends on the specific vehicle engine platform 5 in aftermarket embodiments.

In further reference to FIG. 4, the wiring harness 18 of the engine control device 1 is configured to connect the sobriety measuring device 2 to the ECP 12. Typically, the sobriety measuring device 2 is configured as an aftermarket component. The sobriety measuring device 2 can be produced standalone or in tandem with the engine control device 1. The sobriety measuring device 2 comprises a sobriety processor 20 and a signal-out port 22; the sobriety processor 20 being electronically connected to the signal-out port 22.

In yet further reference to FIG. 4, the wiring harness 18 of the engine control device 1 is terminally connected to the signal-out port 22. More specifically, an electrical connector of the wiring harness 18 of the engine control device 1 is connected to the signal-out port 22. Alternatively, the wiring harness 18 of the engine control device 1 can be directly connected to the sobriety processor 20. Such an embodiment is more plausible when manufacturing the engine control device 1 in tandem with the sobriety measuring device 2.

The ECP 12 allows for the management of electronic signals throughout the sobriety ignition interlock system and the execution of pre-programmed commands. More specifically, the ECP 12 is configured to receive a sobriety signal from the sobriety measuring device 2. Furthermore, the ECP 12 is configured to intercept an engine signal transmitted from the engine sensor assembly 4 to the ECU 3, and manipulate the engine signal in response to the sobriety signal.

Figure 10:
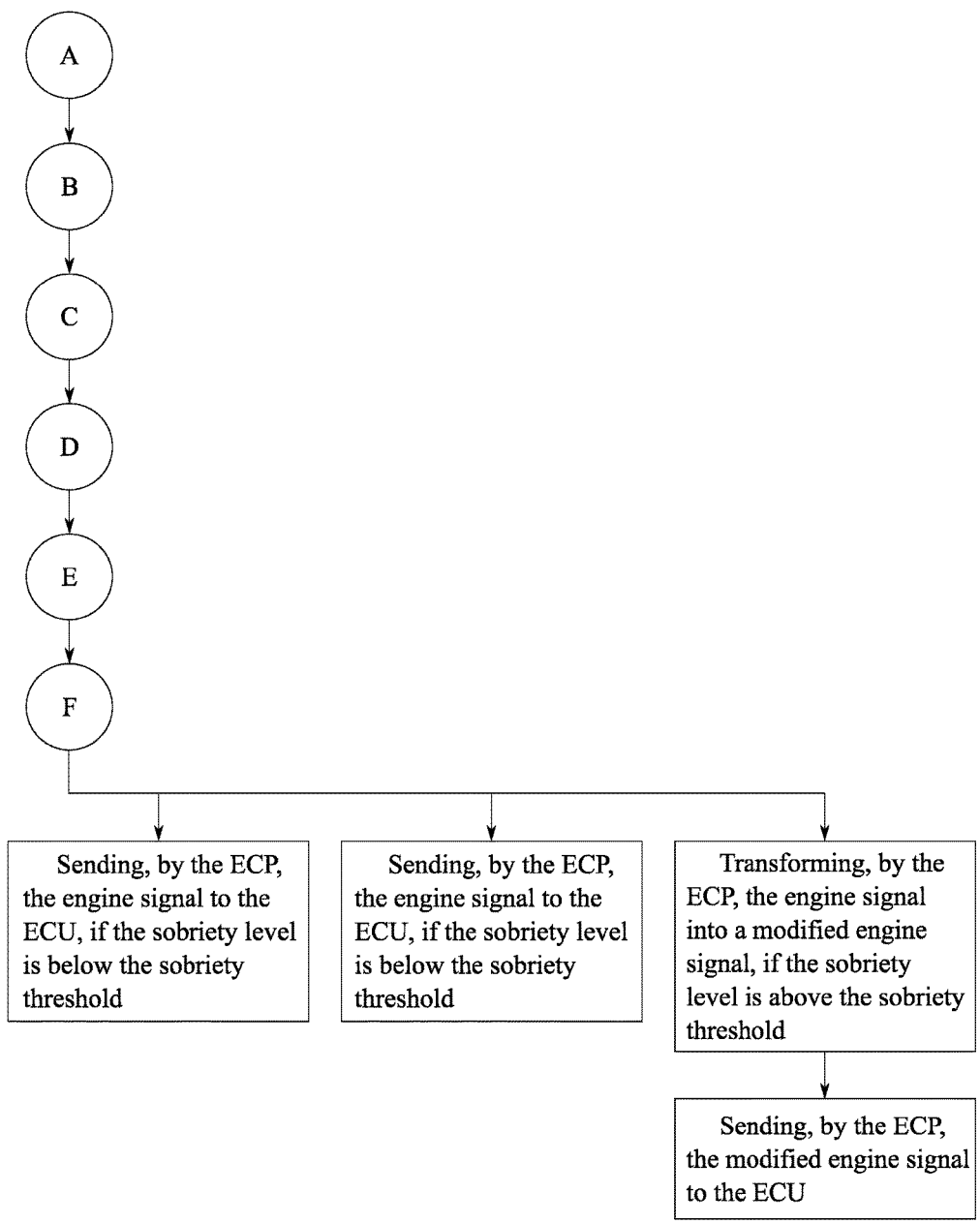
FIG. 10 is a flowchart thereof, further depicting steps for manipulating the engine signal according to the sobriety level.
Figure 12:
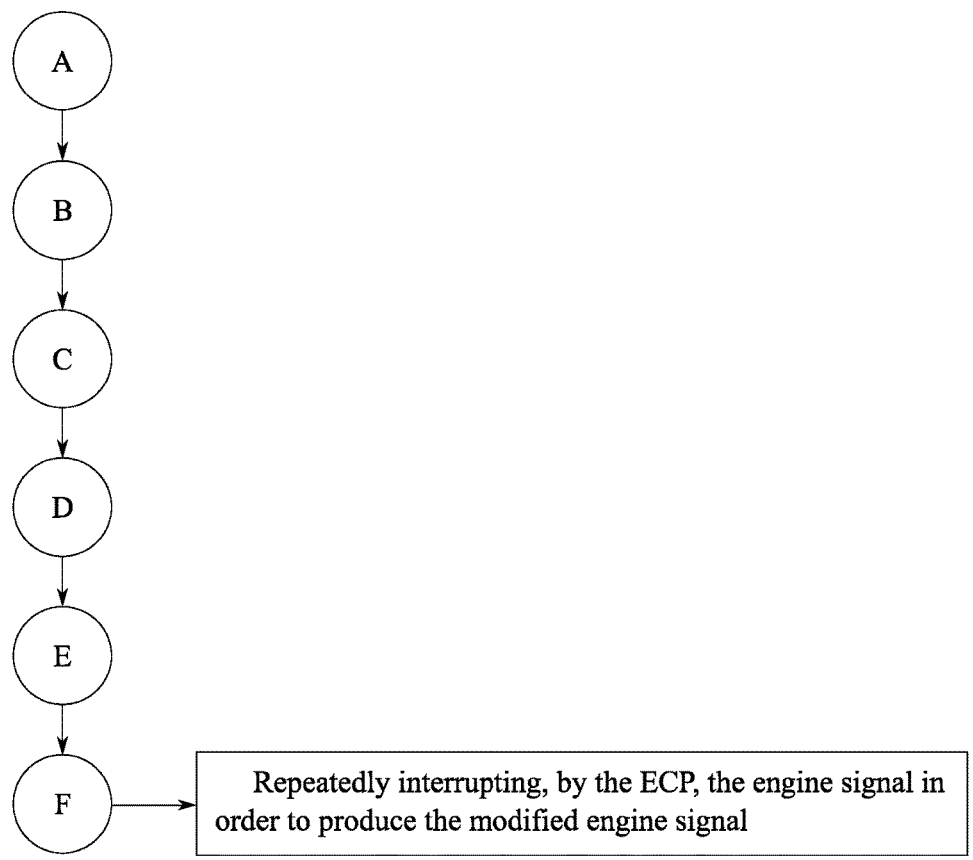
FIG. 12 is a flowchart thereof, further depicting a process for creating the modified engine signal.

The engine signal may be manipulated in multiple ways, as referenced in FIG. 10. In one embodiment, the ECP 12 is configured to terminate the engine signal. In other embodiments the ECP 12 is configured to transform the engine signal into a modified engine signal, and transmit the modified engine signal to the ECU 3. One method requires the ECP 12 to transform the engine signal by altering the voltage of the engine signal. Another method requires the ECP 12 to interrupt signal pulses of the engine signal, as depicted in FIG. 12. The ECP 12 may continuously monitor the engine sensor assembly 4 in order to manipulate the engine signal as needed.

The sobriety processor 20 is configured to produce the sobriety signal according to the results of a sobriety test carried out by the vehicle driver. The sobriety test is carried out in order to determine a sobriety level of the vehicle driver, wherein the sobriety level is utilized to determine the sobriety signal. The sobriety test can be carried out in different ways, depending on the embodiment of the present invention.

Figure 5:
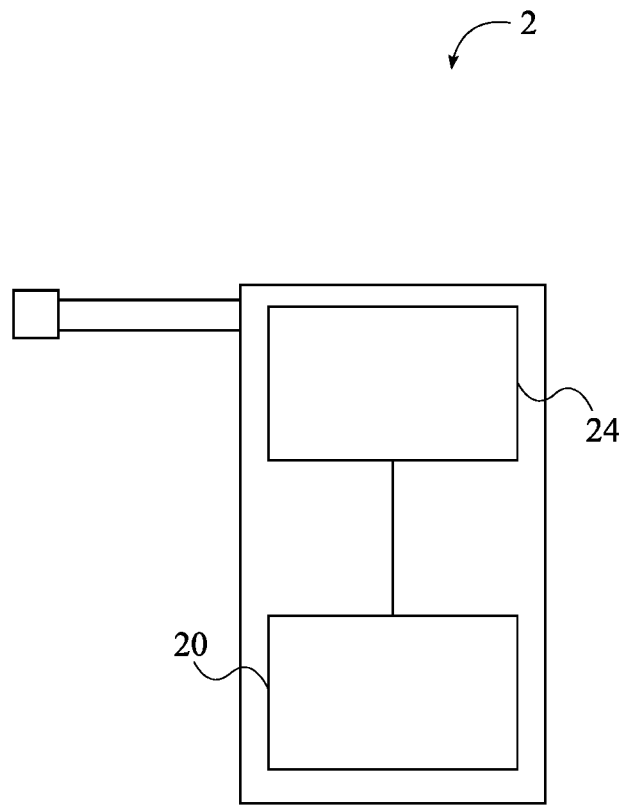
FIG. 5 is a diagram depicting the sobriety measuring device, wherein a blood alcohol content (BAC) sensor is electronically connected to the sobriety processor and utilized to determine the sobriety level.

In reference to FIG. 5, in one embodiment of the present invention, the sobriety measuring device 2 further comprises a blood alcohol content (BAC) sensor 24 and a breath opening. The BAC sensor 24 is positioned adjacent to the breath opening and is electronically connected to the sobriety processor 20. The sobriety processor 20 is configured to calculate the sobriety level from a sensor reading derived from the BAC sensor 24, and then produce the sobriety signal according to the sobriety level.

To obtain the sensor reading, the vehicle driver exhales into the breath opening. The BAC sensor 24 then forms the sensor reading, which is relayed to the sobriety processor 20, according to the measured BAC of the vehicle driver. The sobriety processor 20 then calculates the sobriety level from the sensor reading. For example, the sensor reading may be a voltage produced by the BAC sensor 24, wherein the voltage corresponds to a particular BAC.

Figure 6:
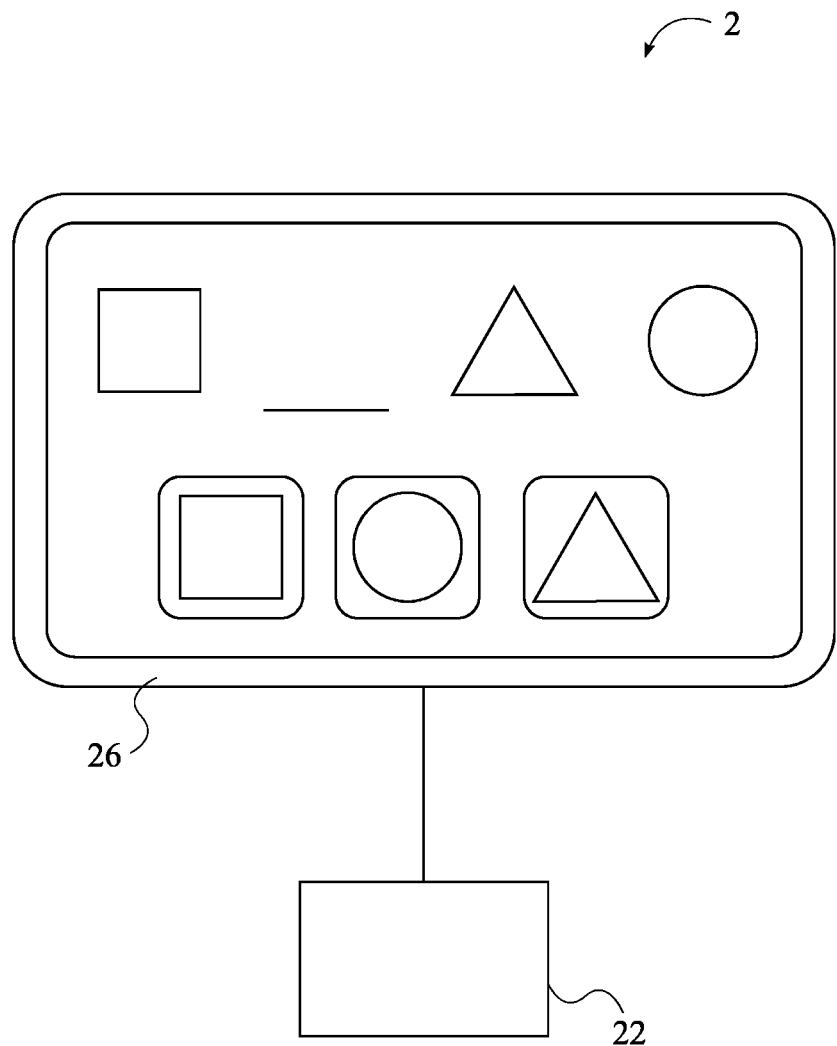
FIG. 6 is a diagram depicting the sobriety measuring device, wherein a haptic input device is electronically connected to the sobriety processor and utilized to determine the sobriety level.

In reference to FIG. 6, in another embodiment of the present invention, the sobriety measuring device 2 further comprises a haptic input device 26. The haptic input device 26 is electronically connected to the sobriety processor 20, wherein the sobriety processor 20 is configured to calculate the sobriety level derived from a driver input into the haptic input device 26, and then produce the sobriety signal according to the sobriety level. The haptic input device 26 may be a touchscreen, joystick, button, or other physical user interface.

To obtain the sensor reading, the vehicle driver interacts with the haptic input device 26. The haptic input device 26 receives the driver input, which is then relayed to the sobriety processor 20. The sobriety processor 20 analyzes the driver input and then calculates the sobriety level from the driver input. The sobriety test, and in turn the driver input that is required, can be configured to measure the cognitive abilities or motor function of the vehicle driver.

In one embodiment, the haptic input device 26 is utilized to measure cognitive abilities of the vehicle driver, wherein the sobriety test measures the ability to reason and/or observe. Characters (e.g. numerals, letters, shapes), various colors, and/or visual movements are displayed on a screen and the vehicle driver is required to input appropriate responses (e.g. to complete a sequence), as depicted in FIG. 6. Proper responses would require the vehicle driver to engage in a degree of recognition and unassisted insight to pass.

One or more visual tests may be performed in order for the vehicle driver to pass the sobriety test. Baselines for particular visual tests would be established by professionals and would be stored on the sobriety processor 20 or a connected memory device. The particular visual tests would be presented to the vehicle driver and the responses would be compared to the baselines, while additional tests would present visuals not before seen by the vehicle driver. The sobriety processor 20 receives and analyzes the responses to both sets of tests, and determines whether or not the vehicle driver is allowed to operate the vehicle.

In other embodiments, the haptic input device 26 is utilized to measure motor functions or the agility of the vehicle driver. One example requires the vehicle driver to use a finger to follow a shape or figurine that randomly moves across a touchscreen for a pre-determined length of time. Another example requires the vehicle driver to follow a number of finger patterns displayed on the touchscreen. Yet another example requires the vehicle driver to tap the screen within a short time interval when a shape appears on screen. Instead of using a touchscreen a button could be provided, wherein the user depresses the button and quickly releases the button when shown a command signal.

The motor function tests measure the reaction time of the vehicle driver, which is then utilized to determine whether or not the vehicle driver should be allowed to operate the vehicle. Similar to the cognitive tests, the motor function tests also utilize baselines that are established by professionals and stored on the sobriety processor 20 or a connected memory device, prior to the operation of the vehicle. The responses recorded throughout the motor function tests are recorded and compared by the sobriety processor 20 to the baselines to establish whether or not the vehicle driver is allowed to operate the vehicle.

In some embodiments, both the BAC sensor 24 and the haptic input device 26 may be utilized to determine the sobriety level of the vehicle driver, wherein the vehicle driver must pass both types of sobriety tests in order to operate the vehicle. For example, the vehicle driver may have a BAC below the legal limit, however, if the vehicle driver is unable to adequately complete the cognitive or motor function tests, then the vehicle driver will not be allowed to operate the vehicle. As an alternative example, the vehicle driver may pass the cognitive and/or motor function tests, but have a BAC above the legal limit, and therefore not be permitted to operate the vehicle.

Figure 2:
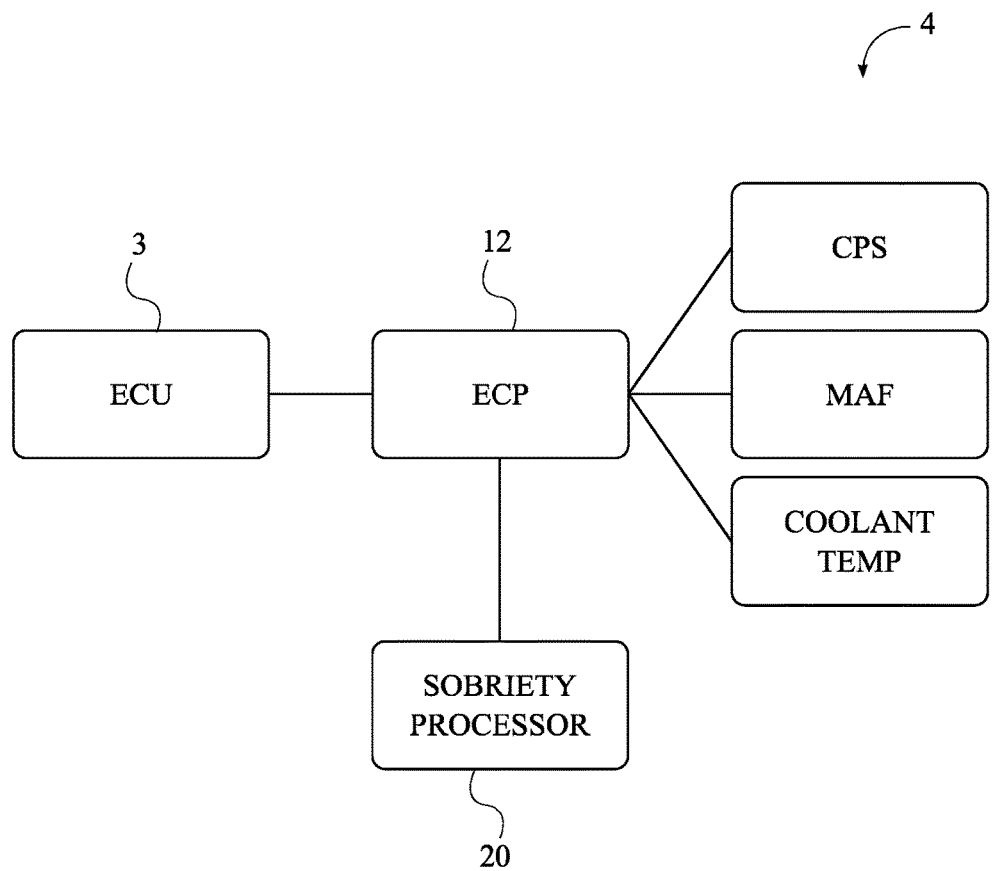
FIG. 2 is a diagram depicting the electronic connections between the engine control processor (ECP) and each of the ECU, the engine sensor assembly, and the sobriety measuring device for managing the available power of the vehicle engine.

In reference to FIG. 2, in order to manage the available power of the vehicle engine, the ECP 12 is electronically connected in between the ECU 3, the engine sensor assembly 4, and the sobriety processor 20. The engine sensor assembly 4 continuously monitors parameters of the vehicle engine and is in communication with the ECU 3 through the ECP 12. The ECP 12 is able to intercept and modify transmissions from the engine sensor assembly 4 to the ECU 3 upon instruction from the sobriety processor 20.

Figure 7:
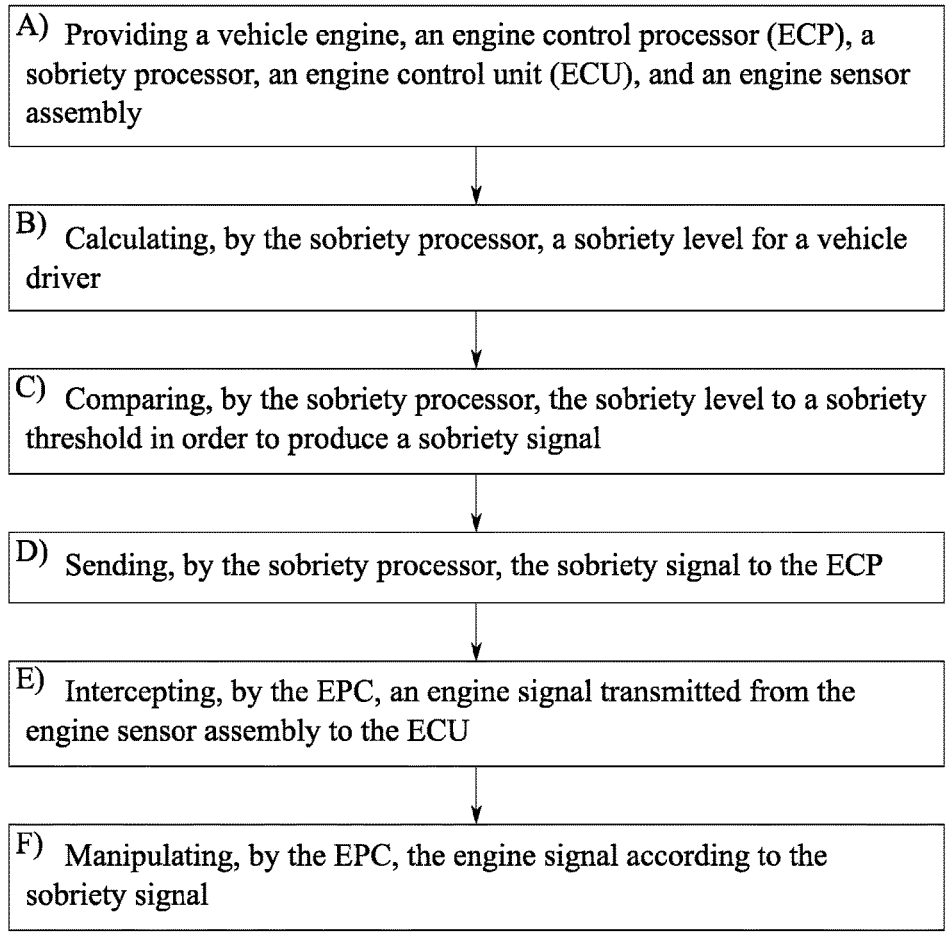
FIG. 7 is a flowchart depicting the steps for managing the available power of the vehicle engine, wherein a sobriety level is determined in order to manipulate an engine sensor intercepted from the engine sensor assembly to the ECU.
Figure 8:
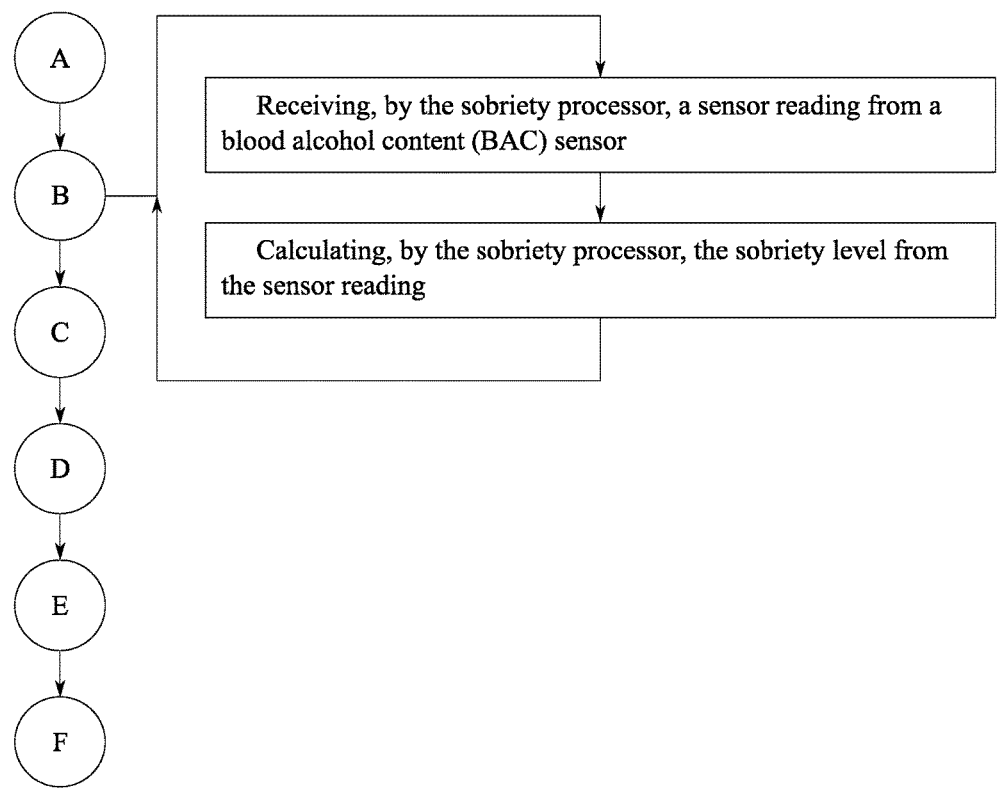
FIG. 8 is a flowchart thereof, further depicting steps of determining the sobriety level by utilizing the BAC sensor.
Figure 9:
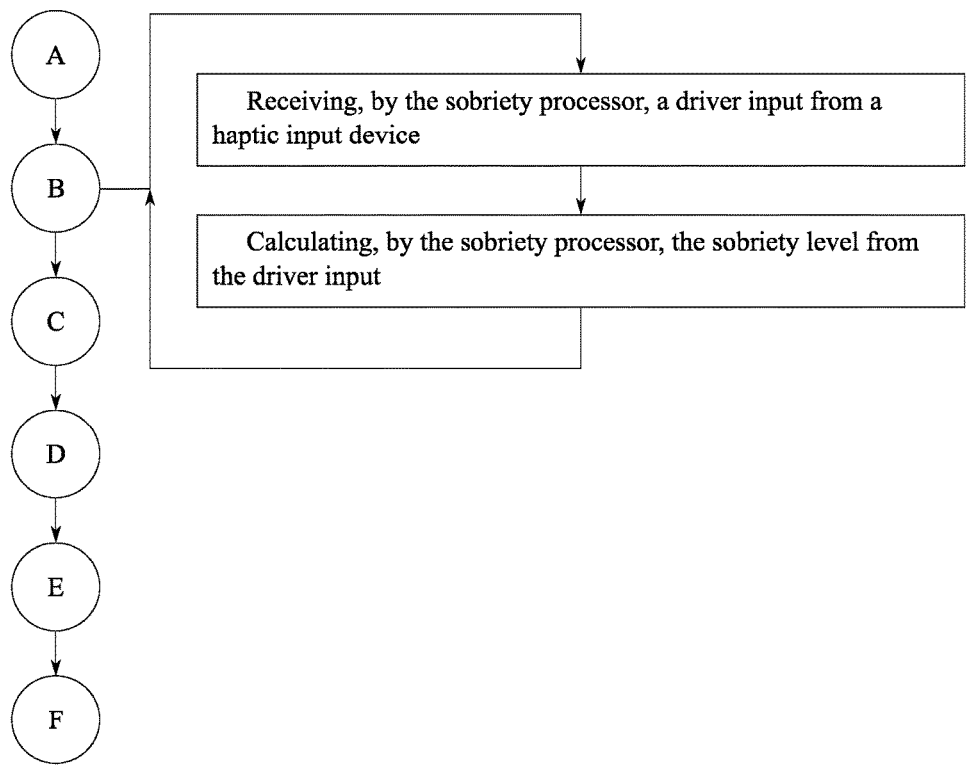
FIG. 9 is a flowchart thereof, further depicting steps for determining the sobriety level by utilizing a driver input entered into the haptic input device.

In reference to FIG. 8-9, the sobriety processor 20 first receives either the sensor reading from the BAC sensor 24 or the driver input from the haptic input device 26. The sobriety test can be performed prior to ignition of the vehicle engine, or while the vehicle engine is running. In reference to FIG. 7, the sobriety processor 20 then calculates the sobriety level (step B) for the vehicle driver from either the sensor reading or the driver input. Once the sobriety processor 20 has calculated the sobriety level, the sobriety processor 20 compares the sobriety level to a sobriety threshold in order to produce the sobriety signal (step C).

The sobriety threshold is pre-programmed and is stored on the sobriety processor 20 or on a memory device connected to the sobriety processor 20. The sobriety threshold is utilized to determine whether or not the vehicle may be operated, wherein the sobriety threshold sets the upper limit on how inebriated the vehicle driver may be and still be allowed to operate the vehicle. As laws and regulations vary from state to state, the sobriety threshold may be set at different limits.

In reference to FIG. 7, once the sobriety processor 20 has produced the sobriety signal, the sobriety processor 20 sends the sobriety signal to the ECP 12 (step D). The ECP 12 then manipulates the engine signal according to the sobriety signal (step F), wherein the engine signal is first intercepted by the ECP 12 (step E). The ECP 12 continuously intercepts, or monitors, the engine signal that is transmitted from the engine sensor assembly 4 to the ECU 3, such that the ECP 12 can control the signal received by the ECU 3 and in turn control the available power of the vehicle engine.

The manipulation of the engine signal depends on the sobriety signal and a current power state of the vehicle engine. In one embodiment of the present invention, the ECP 12 monitors the current state of the vehicle engine and determines the manipulation of the engine signal by processing both the current state and the sobriety signal. In another embodiment of the present invention, the ECP 12 relays the current state to the sobriety processor 20, wherein the sobriety processor 20 produces the sobriety signal according to the current state and the sobriety level.

In reference to FIG. 10, if the vehicle engine is not running, and the sobriety level is above the sobriety threshold, then the ECP 12 terminates the engine signal, wherein the ECU 3 does not receive the engine signal. In this way, the vehicle engine is unable to ignite because the ECU 3 is unable to process the engine signal required for ignition. If the vehicle engine is not running, and the sobriety level is below the sobriety threshold, then the EPC sends the engine signal to the ECU 3 unaltered. In this way, the vehicle engine is able to ignite because the ECU 3 is able to properly process the engine signal as originally sent.

In further reference to FIG. 10, if the vehicle engine is running, and the sobriety level is above the sobriety threshold, then the ECP 12 transforms the engine signal into the modified engine signal in order to reduce the speed of the vehicle. The modified signal is sent from the ECP 12 to the ECU 3, wherein the modified engine signal provides false data to the ECU 3 in order to cause the ECU 3 to slow down or completely stop the vehicle. The ECP 12 may transform the engine signal into the modified engine signal by repeatedly interrupting the engine signal as depicted in FIG. 12, changing the voltage of the engine signal, or by otherwise modifying the engine signal.

Figure 11:
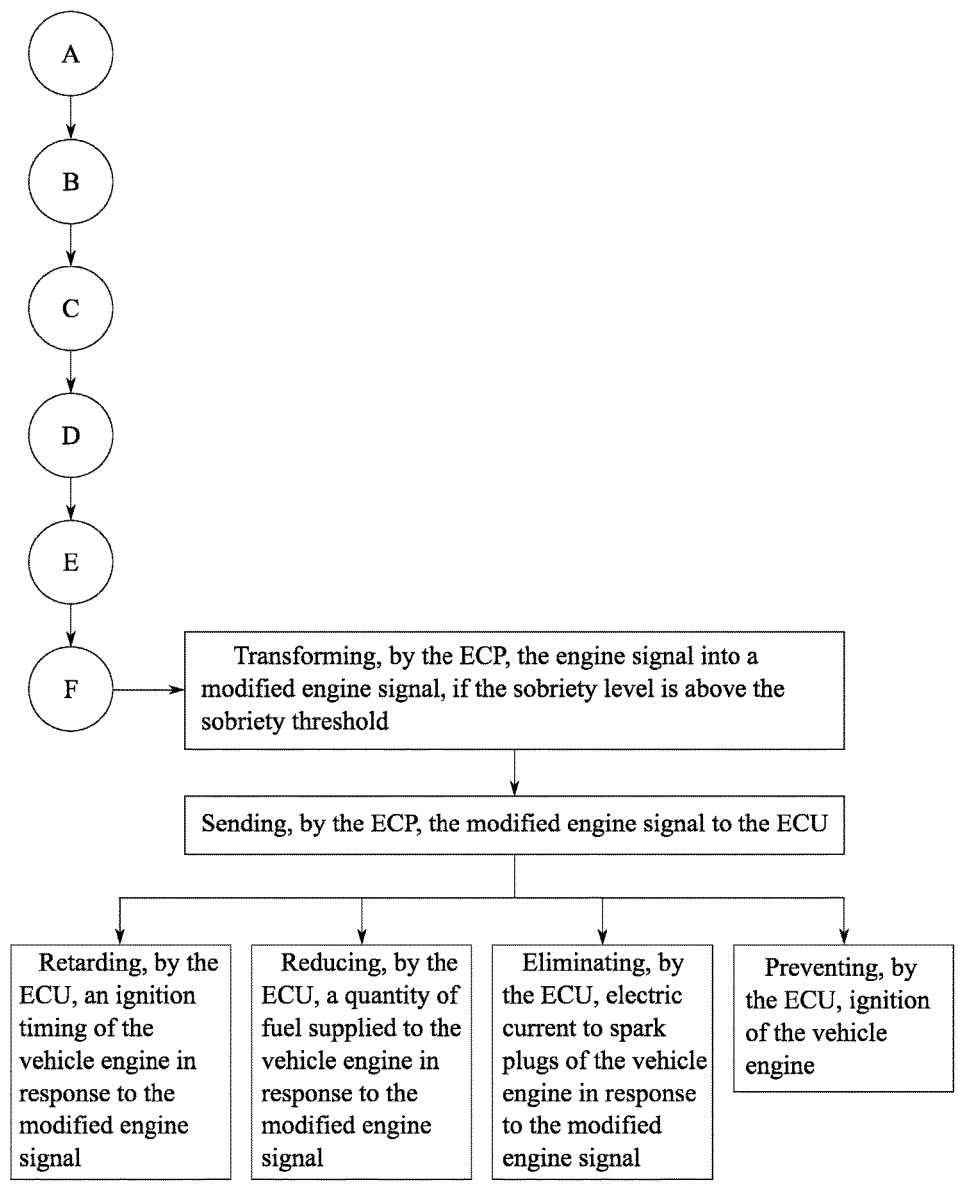
FIG. 11 is a flowchart thereof, further depicting steps for managing the available power of the vehicle engine, by the ECU, according to the modified engine signal produced by the ECP.

In reference to FIG. 11, the modified engine signal can cause the ECU 3 to slow the vehicle in a number of different ways. In one embodiment, the ECU 3 retards an ignition timing of the vehicle engine in response to the modified engine signal. In another embodiment, the ECU 3 reduces a quantity of fuel supplied to the vehicle engine in response to the modified engine signal. In yet another embodiment, the ECU 3 eliminates electric current to spark plugs of the vehicle engine in response to the modified engine signal.

In some embodiments, the modified engine signal may be utilized to control other systems of the vehicle in addition to or in place of the vehicle engine. For example, while driving, if the vehicle driver should fail a sobriety re-test, the ECP 12 can control the ECU 3 to override the stereo or any other in-vehicle distractions that one, especially when intoxicated, can be more easily distracted by. These warnings that consist of very momentary and abrupt power losses will send a powerful message to the vehicle driver. Temporary disabling of the stereo, standalone or in conjunction with a decrease in available engine power, sends the message that the vehicle driver is no longer in full control of the vehicle, reminding the vehicle driver that the consequence of prosecution and legal penalties should be strongly considered. With this feature, the communication to the driver is being physically reinforced by the vehicle in real time. This is far more compelling than just a visible or verbal warning.

The action taken by the ECU 3 in response to the modified engine signal depends on the specific vehicle engine platform 5 and in turn the engine sensor assembly 4. Depending on the vehicle, the engine sensor assembly 4 may include at least one of a mass air sensor (MAF), a crankshaft position sensor (CPS), a camshaft position sensor, a throttle position sensor, a manifold pressure sensor, an air intake temperature sensor, an ambient air temperature sensor, a coolant sensor, or an engine oil temperature sensor.

In one embodiment, the engine sensor assembly 4 includes a CPS. If the sobriety level is above the sobriety threshold, then the ECP 12 does not allow the engine signal from the CPS to be passed to the ECU 3. In turn, the ECU 3 does not recognize any crankshaft rotations for the vehicle engine. Therefore, the ECU 3 either does not provide any electrical current to the spark plugs, or does not allow any fuel to be provided to the vehicle engine.

Further, in the event that the sobriety level has not exceeded the sobriety threshold, and the vehicle engine is allowed to start, the vehicle driver may be required to perform a sobriety re-test. If the vehicle driver either fails to comply with the required sobriety re-test, or when re-tested, fails to indicate legal sobriety, using only the CPS, the ECU 3 can be exclusively used to limit the available power of the vehicle engine in many cases.

Most CPS units utilize inductive pickup via a magnet to produce the engine signal that is sent to the ECU 3, wherein the engine signal correlates with engine revolutions per minute (RPM). As power reductions to the vehicle engine are commanded by pre-set determination and programming, the modified engine signal effectively reduces the value of the engine signal and thus reduces the engine RPM observed by the ECU 3. The ECU 3 receives from the ECP 12 missing signal patterns that are a fractional quotient of the full and uninterrupted signal from the CPS, such that a significant portion of the ignition events are cancelled by the ECU 3. Additionally, the ECU 3 may cancel fuel injector events, reducing fuel to the vehicle engine.

The ECU 3 is the brain, or computer processor, of the vehicle engine, and in order for mandated emissions compliance, the ECU 3 is programmed to read numerous sensors, most of which are not relied on as inputs for the method of the present invention. The ECU 3 must sync all input signals with proper pre-programmed look up tables, algorithms, and acceptable engine parameters, such that correct outputs are generated to the vehicle engine for proper engine operation. However, the inventive aspect of generating a partial pulse value (i.e. the modified engine signal) as interpreted by the ECU 3, such that the ECU 3 reduces fuel and spark frequency to a spark ignited internal combustion engine is unique to the field of breath alcohol ignition interlock devices (BAIIDs).

Further, with differing electronic pulse values generated by the ECP 12, compression-ignited engines, or diesel engines, also significantly reduce power output because less fuel is delivered. In spite of the lack of any ignition system integrated into compression-ignited engines, the opportunity for pre-ignition is not present as compression-ignited engines are configured by design to already pre-ignite continuously during proper combustion and operation.

Accordingly, when a significant quantity of fuel is removed in compression-ignited engines, power output is reduced dramatically and exhaust valve and exiting gas temperatures are generally reduced. Diesel engines utilizing the method of present invention to reduce power through the intercepting of the engine signal from the CPS (or other sensor utilized by the engine sensor assembly 4), reduce engine power proportionally with the intensity of the interruption to the engine signal as perceived by the ECU 3. So, when the sobriety level of the vehicle driver has been found to be over the sobriety threshold, engine power can be controlled, limited, reduced, or safely shut off completely when desired by generating the modified engine signal.

Figure 15:
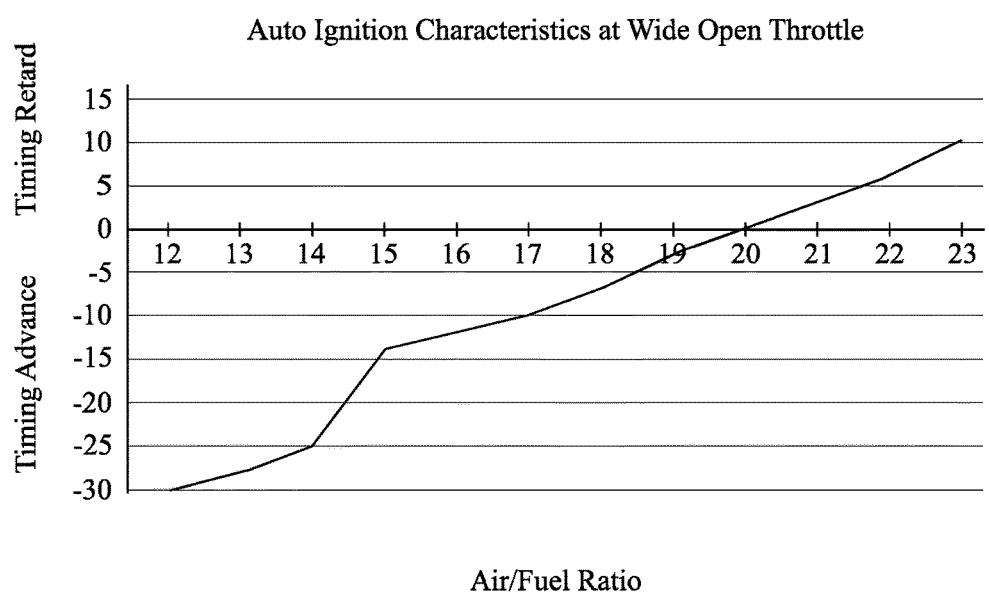
FIG. 15 is a line graph depicting the required spark advance or retard at wide open throttle so as to avoid auto ignition and/or pre-ignition, for a typical spark ignited internal combustion engine.

FIG. 15 is a line graph that illustrates a typical emission equipped and compliant spark ignited engine in relation to reduction of the ratio of the quantity of combustion fuel to the quantity of combustion air, or the "air fuel ratio", so as to avoid pre-ignition at various air fuel ratios. All FIG. 15 line graph plotted values are at wide open throttle (W.O.T.). The air fuel ratios are plotted at W.O.T. as the vehicle driver that has failed the sobriety re-test, or has failed to take the sobriety re-test, may likely be motivated to try and overcome the power reduction to the vehicle engine by pushing the accelerator pedal much further open, or to the floor, therefore fully opening the engine intake throttle. This allows the full quantity of intake air to enter the engine, but with the significant reduction of fuel to the vehicle engine due to the modified engine signal received by the ECU 3. Therefore, the air fuel ratio in the combustion chamber becomes increasingly lean and the propensity for auto ignition (detonation or pre-ignition) becomes far greater as fuel quantity is reduced but air quantity is unchanged or increased.

It is commonly known that meaningful pre-ignition or detonation can and will typically produce significant engine damage and in many cases, complete engine destruction. In spark ignited internal combustion engines, when "auto ignition" occurs before scheduled ignition in the cylinder, significant oxides of nitrogen (NOX) are produced by the improper combustion process and emitted out the tailpipe as harmful emission discharge. Furthermore, auto ignition before scheduled ignition presents the possibility of engine failure.

The left side of the line graph depicted in FIG. 15 indicates that when the air fuel ratio contains more fuel by weight than air by weight, or is "richer" than the stoichiometric ratio, the vehicle engine will tolerate significant ignition timing advance and produce more horsepower. However, when the air to fuel ratios are "leaner" than the stoichiometric ratio, significant retarding of ignition timing must be utilized so that engine damaging pre-ignition, detonation does not occur, and non-complying Environmental Protection Agency (EPA) designated emission levels are not produced.

In the preceding aspect of the present invention, the engine signal of only one CPS is required to be manipulated, such that the engine signal is not passed through to the ECU 3, preventing ignition of the vehicle engine. Additionally, the power of the vehicle engine can also be significantly reduced at will by rapidly interrupting the engine signal, eliminating some pulses of the engine signal, reducing the voltage of the engine signal, changing the resistance of the engine signal, or otherwise altering the engine signal to lead the ECU 3 to reduce fuel supply and power. Further, with the monitoring of the air fuel ratio by exhaust oxygen sensors, the ECU 3 may have adequate offset range as programmed, so as to maintain a safe air fuel ratio and avoid pre-ignition, detonation and harmful emissions.

An additional aspect of the present invention that also uses one CPS and no other sensors to reduce power, is the combination of ignition timing retard with the modified engine signal that determines the observed engine RPM. This inventive aspect momentarily retards or reduces the ECU 3 commanded ignition timing, with momentary and repeated reductions of timing, and rapid restorations. These fluctuating ignition retarding cycles, are applied for a fraction of a second, or up to several seconds, based on dynamic operation of varying engine families and the specific operating characteristics of each engine family.

If the ignition timing of a spark ignited internal combustion engine is significantly reduced, the vehicle engine output power is also reduced. However, if fuel delivery quantity is not reduced by a significant manner, the air fuel ratio becomes excessively rich and misfiring in the combustion cylinders may occur. Furthermore, within a short time period, unburned fuel will dilute the lubricating oil film from the cylinder walls causing significant piston ring friction and wear to the vehicle engine. However, as provided by the present invention, it has been discovered that when the ignition timing is momentarily retarded and restored before misfire occurs, the exhaust gas temperatures are limited to a reliable threshold and lubrication of the piston rings are maintained. Therefore, the net effective output power of the vehicle engine is significantly reduced, and accordingly, the vehicle speed is significantly limited.

Figure 13:
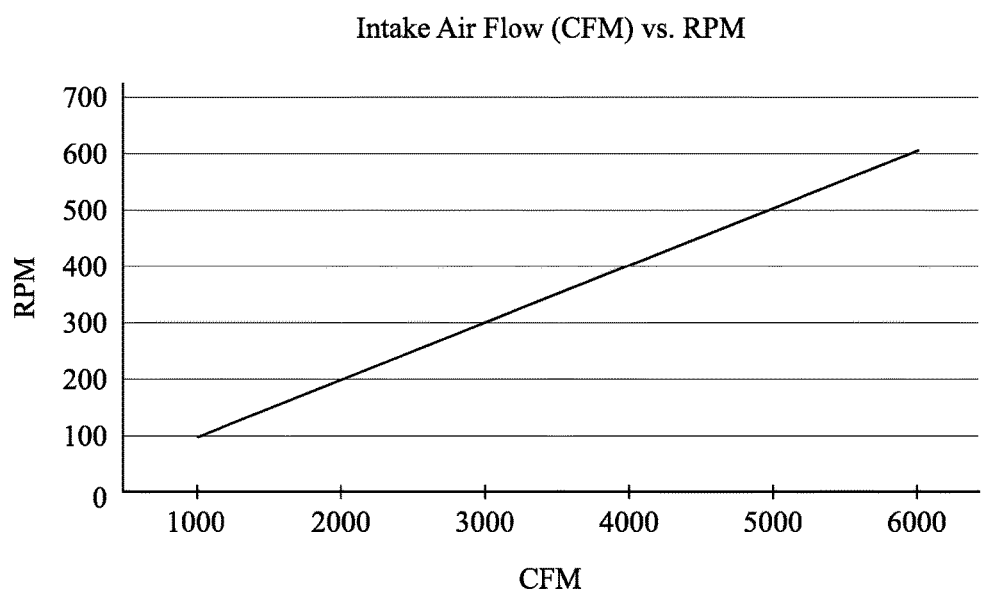
FIG. 13 is a line graph plotting the engine air intake versus engine revolutions per minute for a typical 300 horsepower gasoline internal spark combustion engine.

Another embodiment of the present invention is reliant on the combination of a CPS, or substitute rotating sensor, and a MAF. Referring to FIG. 13, the intake air quantity, as measured in cubic feet per minute (CFM), linearly increases in relation to engine RPM. FIG. 13 depicts a typical 300 horsepower spark ignited internal combustion engine with a volumetric efficiency (VE) of about 85%. Intake air is measured by the MAF, wherein the MAF produces an engine signal corresponding to the volume of intake air. When the vehicle engine is operating, the quantity of air passing through the MAF is directly correlated to the actual horsepower that an internal combustion spark ignited, or compression ignited, engine is actually producing.

It should be noted that each engine family is calibrated at the time of manufacture, such that the MAF produces a known signal value that directly correlates to that actual produced horsepower of the vehicle engine, at any given RPM. However, the correlation to actual horsepower produced is predicated on optimal and proper ignition timing and advance and the correct air fuel ratio, and in the case of compression ignited engines, the proper air fuel ratio.

In this embodiment, there are predetermined relationships of timing retard, through the delay in the engine signal of the CPS provided to the ECU 3, and a reduction in the signal values of the engine signal from the MAF to the ECU 3, via the ECP 12. For minor reductions in engine power, either the values of the engine signal of the MAF can be reduced or the engine signal of the CPS can be delayed.

If only the signal values of the engine signal from the MAF are reduced, the combustion mixture will become considerably lean, and engine damage and harmful tailpipe discharge will occur. Alternatively, if just the signal pulses of the engine signal from the CPS are delayed or retarded, the combustion mixture will become considerably rich and cause spark plugs to miss-fire, and excessive fuel may dilute the cylinder walls, prematurely wearing the piston rings, while excessive un-burned hydrocarbons and other harmful tailpipe discharge will be emitted.

Thus in some aspects of operation, either the engine signal from the MAF or the CPS could be conditioned exclusively by the ECP 12 for minor power reduction events. But when more significant engine power reduction is needed, both the engine signal of the MAF and the engine signal of the CPS, in communication with the ECP 12, allow the engine timing to be reduced, and the rich air fuel ratio that is the result, to be modulated and equalized by the reduction of engine fuel supply.

Figure 14:
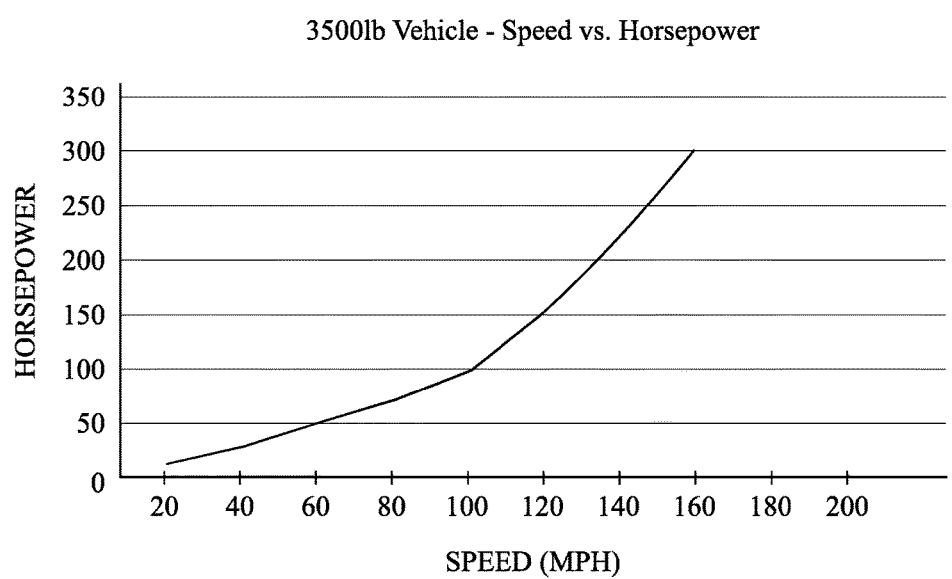
FIG. 14 is a line graph plotting the relation of horsepower to potential top speed for a typical 3500 pound vehicle.

FIG. 14 shows a line graph of the relationship between engine horsepower and potential top speed for a typical 3500 pound vehicle. As FIG. 14 indicates, it requires exponentially more horsepower to reach higher vehicle speeds. However, the line graph also emphasizes just how little horsepower can be required to reach potentially deadly speeds, in the event that an intoxicated driver is allowed to continue to drive, as is commonly allowed with the operation of current BAIIDs on the roads today. FIG. 14 strongly illustrates that only a small percentage of available horsepower will allow a vehicle to maintain highway speeds.

It should be understood that in order to effectively minimize vehicle speed, the level of power reduction may easily be more that 90% power reduction. For low horsepower equipped vehicles, a lesser amount would be effective and for high horsepower performance vehicles, power reduction of more than 95% would sometimes be the only effective way to maintain public safety on the roads.

The present invention has multiple benefits, attributes, and significant adaptability to very effectively block an engine from starting when needed, or reduce engine power to reduce speed related accidents caused by intoxicated drivers.

Although the invention has been explained in relation to its preferred embodiment, it is to be understood that many other possible modifications and variations can be made without departing from the spirit and scope of the invention as hereinafter claimed.

What is claimed is:

1. An engine control device for use in a sobriety ignition interlock system comprises:
   a housing, an engine control processor (ECP), an electronic input port for connecting to an engine sensor assembly, an electronic output port for connecting to an engine control unit (ECU), and a wiring harness for connecting to a sobriety measuring device;
   the ECP being positioned within the housing;
   the electronic input port and the electronic output port being mounted into the housing;
   the ECP being electronically connected in between the electronic input port, the electronic output port, and the wiring harness;
   the ECP being configured to receive a sobriety signal from the sobriety measuring device;
   the ECP being configured to intercept an engine signal transmitted from the engine sensor assembly to the ECU; and
   the ECP being configured to manipulate the engine signal in response to the sobriety signal.

2. The engine control device for use in a sobriety ignition interlock system as claimed in claim 1 comprises:
   the ECP being configured to terminate the engine signal, wherein the engine signal is not relayed to the ECU.

3. The engine control device for use in a sobriety ignition interlock system as claimed in claim 1 comprises:
   the ECP being configured to transform the engine signal into a modified engine signal; and
   the ECP being configured to transmit the modified engine signal to the ECU.

4. The engine control device for use in a sobriety ignition interlock system as claimed in claim 3, wherein the ECP is configured to alter the voltage of the engine signal.

5. The engine control device for use in a sobriety ignition interlock system as claimed in claim 3, wherein the ECP is configured to interrupt signal pulses of the engine signal.

6. The engine control device for use in a sobriety ignition interlock system as claimed in claim 1 comprises:
   the ECP being configured to continuously monitor the engine sensor assembly.

7. The engine control device for use in a sobriety ignition interlock system as claimed in claim 1 comprises:
   both the electronic input port and the electronic output port corresponding to a specific vehicle engine platform.

8. A sobriety ignition interlock system for a vehicle comprises:
   an engine control device, a sobriety measuring device, an engine control unit (ECU), and an engine sensor assembly;
   the engine control device comprises an engine control processor (ECP);
   the sobriety measuring device comprising a sobriety processor;
   the ECP being electronically connected in between the sobriety processor, the ECU, and the engine sensor assembly;
   the sobriety processor being configured to produce a sobriety signal;
   the ECP being configured to receive the sobriety signal from the sobriety processor;
   the ECP being configured to intercept an engine signal transmitted from the engine sensor assembly to the ECU; and
   the ECP being configured to manipulate the engine signal in response to the sobriety signal.

9. The sobriety ignition interlock system for a vehicle as claimed in claim 8 comprises:
   the engine control device further comprising an electronic output port, an electronic input port, and a wiring harness; and
   the ECP being electronically connected in between the electronic input port, the electronic output port, and the wiring harness.

10. The sobriety ignition interlock system for a vehicle as claimed in claim 9 comprises:
    the ECU comprising a wiring harness; and
    the wiring harness of the ECU being terminally connected to the electronic output port.

11. The sobriety ignition interlock system for a vehicle as claimed in claim 9 comprises:
    the engine sensor assembly comprising a wiring harness; and
    the wiring harness of the engine sensor assembly being terminally connected to the electronic input port.

12. The sobriety ignition interlock system for a vehicle as claimed in claim 9 comprises:
    the sobriety measuring device further comprising a signal-out port;
    the signal-out port being electronically connected to the sobriety processor; and
    the wiring harness of the engine control device being terminally connected to the signal-out port.

13. The sobriety ignition interlock system for a vehicle as claimed in claim 8 comprises:
    the ECP being configured to terminate the engine signal, wherein the engine signal is not relayed to the ECU.

14. The sobriety ignition interlock system for a vehicle as claimed in claim 8 comprises:
    the ECP being configured to transform the engine signal into a modified engine signal; and
    the ECP being configured to transmit the modified engine signal to the ECU.

15. The sobriety ignition interlock system for a vehicle as claimed in claim 14, wherein the ECP is configured to alter the voltage of the engine signal.

16. The sobriety ignition interlock system for a vehicle as claimed in claim 14, wherein the ECP is configured to interrupt signal pulses of the engine signal.

17. The sobriety ignition interlock system for a vehicle as claimed in claim 8 comprises:
  the ECP being configured to continuously monitor the engine sensor assembly.

18. The sobriety ignition interlock system for a vehicle as claimed in claim 8 comprises:
  the sobriety measuring device further comprising a blood alcohol content (BAC) sensor;
  the BAC sensor being electronically connected to the sobriety processor;
  the sobriety processor being configured to calculate a sobriety level from a sensor reading derived from the BAC sensor; and
  the sobriety processor being configured to produce the sobriety signal according to the sobriety level.

19. The sobriety ignition interlock system for a vehicle as claimed in claim 8 comprises:
  the sobriety measuring device further comprising a haptic input device;
  the haptic input device being electronically connected to the sobriety processor;
  the sobriety processor being configured to calculate a sobriety level derived from a driver input into the haptic input device; and
  the sobriety processor being configured to produce the sobriety signal according to the sobriety level.

* * * * *